United States Patent [19]

Gotto

[11] Patent Number: 5,276,142

[45] Date of Patent: Jan. 4, 1994

[54] **PROCESS FOR PURIFICATION OF A 69000 DALTON ANTIGENIC PROTEIN FROM *BORDETELLA PERTUSSIS***

[75] Inventor: John W. Gotto, Suffern, N.Y.

[73] Assignee: American Cyanamid Company, Wayne, N.J.

[21] Appl. No.: 448,777

[22] Filed: Dec. 11, 1989

[51] Int. Cl.$^5$ .............. A61K 39/10; C07K 3/02; C07K 3/20; C07K 15/04

[52] U.S. Cl. .............................. 530/413; 424/92; 435/71.2; 530/350; 530/417; 530/825

[58] Field of Search .............. 424/92; 530/403, 405, 530/406, 413, 417, 419, 420, 421, 423, 424, 425, 350, 825; 435/71.1, 71.2, 71.3

[56] References Cited

U.S. PATENT DOCUMENTS

| | | | |
|---|---|---|---|
| 4,220,717 | 9/1980 | Kuo | 424/92 |
| 4,788,058 | 11/1988 | Parton et al. | 424/92 |
| 5,101,014 | 3/1992 | Burns et al. | 530/395 |

FOREIGN PATENT DOCUMENTS

| | | |
|---|---|---|
| 0162639 | 11/1985 | European Pat. Off. |
| 0310317 | 9/1987 | European Pat. Off. |

OTHER PUBLICATIONS

Gupta et al., Vaccine, vol. 4, No. 3, pp. 185–190 (1986).
Weiss, 1986, Ann. Rev. Microbiol, 40:661–686 Virulence Factors of *Bordetella pertussis*.
Novotny, 1985, Dev. Biol Stand, 61:27–41 Bordetella Adenylate Cyclase.
Novotny, 1985, Infect Immun, 50:190–198 Evaluation of *Bordetella bronchiseptica* Vaccines.
Montaraz, 1985, Infect. Immun, 47:744–751 Identification of a 68-Kilodalton Protective Protein.
Novotny, 1985, Infect. Immun, 50:199–206 Adenylate Cyclase Activity of a 68,000.
Aoyama, 1989, Am. J. Dis. Child, 143:655–59 Efficacy and Immunogenicity of Acellular Pertussis.
Shahin, 1990, J. Exp. Med. 171:63–73 Characterization of the Protective Capacity.
Brennan, 1988, Infect. Immun., 56:3189–95 Identification of a 69-Kilodalton Nonfimbrial Protein.
Charles, 1989, Proc. Natl. Acd. Sci. USA, 86:3554–58 Molecular cloning and Characterization of Protective.
Leininger-Zapata, 1989, Abstr. Amer. Microbiol p. 51 Abr. B-123 Cell Attachment to Putative Adhesins.
Shahin, 1989, Abstr. Amer. Microbiol p. 51 Abr. B-125 Immune Protection Mediated by the 69k Da.
Gould, 1989, Abstr. Amer. Microbiol, p. 51 Abr. B-126 Purification of a 69,000 Da Outer Membrane Protein.
Stainer, 1971, J. Gen. Microbiol, 63:211–220 A Simple Chemically Defined Medium.

*Primary Examiner*—Jeffrey E. Russel
*Attorney, Agent, or Firm*—T. S. Szatkowski

[57] ABSTRACT

A process for extracting and purifying a protein having an apparent molecular weight of about 69,000 daltons from the outer membrane of the bacterium *Bordetella pertussis* is provided. The process includes inactivating *Bordetella pertussis* cells with a bacteriostatic agent, repetitive extraction, and purification of the 69,000 dalton protein from extract by dye ligand chromatography followed by chromatofocusing. The process results in improved yield and stability of the 69,000 dalton protein.

16 Claims, No Drawings

PROCESS FOR PURIFICATION OF A 69000 DALTON ANTIGENIC PROTEIN FROM *BORDETELLA PERTUSSIS*

BACKGROUND OF THE INVENTION

1. Field of the Invention

The invention relates to a process for extracting and purifying a protein having an apparent molecular weight of about 69,000 daltons from the outer membrane of the bacterium *Bordetella pertussis*. The protein so extracted and purified may be utilized as a component of an acellular pertussis vaccine.

2. Description of the Prior Art

The bacterium *Bordetella pertussis* is the causative agent of the serious infectious disease known as pertussis or whooping cough. Vaccines which are used to immunize infants and children are composed of whole cells of *B. pertussis* inactivated with chemical agents or heat. While whole cell vaccines contain the antigenic components necessary to elicit protective immunity, they may also contain substances irrelevant to protection and possibly related to undesirable side effects of immunization.

In an effort to minimize any undesirable side effects of immunization with whole cell vaccines, the pathogenic mechanisms of *B. pertussis* have been studied to determine which antigenic components contribute to protective immunity. The specific antigens so identified thus could be included in an acellular vaccine which would confer immunity to disease without introducing irrelevant and possibly undesirable substances in the immunization. A number of antigens have been proposed as acellular vaccine components, for example: lymphocytosis promoting factor (LPF; also known as histamine sensitizing factor, islet activating protein, and pertussis toxin), filamentous hemagglutinin (FHA), and fimbrial agglutinogens. (Weiss, A.A. and Hewlett, E.L., 1986, Ann. Rev. Microbiol., 40:661-686.)

Another antigen, associated with the *B. pertussis* outer membrane, and having an apparent molecular weight of about 69,000 daltons is referred to as the *B. pertussis* 69K protein or P.69. The *B. pertussis* 69K protein is immunologically related to similar proteins, having slight differences in electrophoretic mobility, produced by the human pathogen *B. parapertussis* and the animal pathogen *B. bronchiseptica*. It has been suggested that the 69K protein would be a protective antigen useful as a vaccine component. The correlation between protection against disease and the presence of specific antibodies was first established for the *B. bronchiseptica* 68K protein, and the investigation was later extended to the 69K protein of *B. pertussis* by Novotny et al. (Novotny, P., Chubb, A. P., Cownley, K., Montaraz, J. A., and Beesley, J. E., 1985. Dev. Biol. Stand. 61: 27-41; Novotny, P., Korisch, M., Cownley, K., Chubb, A. P., and Montaraz, J. A., 1985. Infect. Immun. 50: 190-198; Montaraz, J. A., Novotny, P., and Ivanyi J., 1985. Infect. Immun. 47: 744-751; and Novotny, P., Chubb, A. P., Cownley, K., and Montaraz, J. A., 1985. Infect. Immun. 50: 199-206). Others have shown that 69K is protective in certain animal models of pertussis, either by active or passive immunity. Furthermore, antibodies against 69K are present in sera of humans who have recovered from pertussis. The 69K protein has the properties of a *B. pertussis* agglutinogen, and can act as an adhesin, causing attachment to mammalian cells. The 69K protein is expressed coordinately with LPF, FHA, and other specific factors under the control of a genetic locus related to *B. pertussis* virulence, and is expressed only in virulent strains. Finally, the 69K protein has been reported to be a component of an acellular pertussis vaccine successfully utilized in Japan. (Aoyama, J., Murase, Y., Kato, M., Iwai, H., and Iwata, J., 1989, Am. J. Dis. Child. 143: 655-659; Shahin, R. D., Brennan, M. J., Li, Z. M., Meade, B. D., and Manclark, C. R., 1989, J. Exp. Med. (in press); Brennan, M. J., Li, Z. M., Lowell, J. L., Bisher, M. E., Steven, A. C., Novotny, P., and Manclark, C. R., 1988. Infect. Immun. 56: 3189-3195; Charles, I. G., Dougan, G., Pickard, D., Chatfield, S., Smith, M., Novotny, P., Morrissey, P., and Fairweather, N. F., 1989. Proc. Natl. Acad. Sci. USA 86: 3554-3558; Leininger - Zapata, E., Brennan, M. J., Kenimer, J. G., Charles, I., Fairweather, N., and Novotny, P. 1989, Abstr. Amer. Microbiol. p.51, abstr. B-123; and Shahin, R., Brennan, M. J., and Meade, B. D., 1989. Abstr. Amer. Soc. Microbiol. p.51, abstr. B-125.)

In order to employ the 69K protein as a component of an acellular pertussis vaccine, a method is required for the efficient purification of the protein applicable to commercial production scale. Previously described methods, however, have several disadvantages for adaptation to large scale.

Novotny et al (Infection and Immunity 50: 199-206 (1985); EP 0 162 639) describe a method for extracting and purifying 69K protein from whole *B. pertussis* cells. The method described by Novotny et al includes suspending the whole *B. pertussis* cells in water, adjusting to pH3 with a buffer, incubating at 37° C. for approx 18 hours to release proteins including the 69K protein from the whole cells, removing the cells by centrifugation leaving a protein extract, precipitating the protein extract with acetone at −20° C., and centrifuging the precipitate to separate the precipitated proteins from non-proteinaceous material remaining in solution. The resulting protein extract was chromatographed on a DEAE - Trisacyl ion-exchange column and eluted a with salt gradient. Material not retained by the ion-exchange column was subjected to isoelectric focusing with a preparative isoelectic focusing gel or chromatofocusing. Protein containing fractions as recognized by an anti-69K protein monoclonal antibody were then applied to a monoclonal antibody column which was then eluted with 6M urea to produce the 69K protein.

This method would not be conducive to commercial production of the 69K protein, however, because it requires 18 hours for extraction of the protein from cells, utilizes acetone, a dangerous solvent, in the precipitation step, requires an ion-exchange chromatography column run lasting 20 hours, and utilizes a cumbersome preparative isoelectric focusing procedure lasting 16 hours. Further, the resulting protein preparation is not completely purified until after an additional step where it is passed through an affinity column utilizing anti-69K monoclonal antibodies linked to a polymeric support and eluted utilizing a harsh 6M urea. Finally, the protein is unstable throughout the purification process resulting in some degradation of the protein during purification.

Brennan et al [Infection and Immunity 56: 3189-3195 (1988)] also describe a method for extracting and purifying the *B. pertussis* 69K protein from whole *B. pertussis* cells. The method described by Brennan et al includes suspending live *B. pertussis* cells in a phosphate buffered saline solution, incubating at 60° C. for 1 hour to release the proteins from the cells, removing the cells by centrifugation leaving a protein extract and dialyzing the protein extract so obtained in a tris-buffered saline solution which contains the protease inhibitors ethylenediaminetetraacetic acid (EDTA) and phenylmethylsulfonylfluoride (PMSF), and Brij 35, a detergent. The extract is then applied to a fetuin-Sepharose column to remove pertussis toxin, followed by a monoclonal antibody affinity column, which is eluted with 6M urea to produce the 69K protein. As with the method disclosed by Novotny et al, this method is subject to some limitations which make it relatively difficult to carry out efficiently on a commercial scale. For example, comparing the multiple incubation extraction steps of the present invention to the single step of Brennan et al demonstrates that the single incubation extraction step results in a very incomplete extraction of 69K protein from the cells. Further, the method disclosed by Brennan et al would require the large scale use of toxic and expensive chemicals if it were practiced on a commercial scale. Finally, both the Novotny et al and Brennan et al methods require the use of a monoclonal antibody affinity column.

In general, methods employing monoclonal antibody affinity columns are not suited to commercial production because the antibodies are not commercially available and must be generated in a lengthy procedure of immunization followed by hybridoma production and screening. The antibodies must then be purified and linked to the affinity support, all of which is both labor and time consuming. Furthermore, elution from the affinity columns involves high concentrations of urea which is detrimental because urea is a known denaturing agent and can alter protein structural characteristics.

A third method for extracting and purifying 69K protein from whole *B. pertussis* cells is described by Burns et al in U.S. Ser. No. 7/308,864 filed Feb. 10, 1989, now U.S. Pat. No. 5,101,014, and in abstracts of American Society of Microbiology, p. 51, abstract B-126 (1989). This method includes suspending live *B. pertussis* cells in a tris-buffered saline solution which contains PMSF and sodium azide, incubating at 60° C. for 1 hour to release proteins from the cells, removing the cells by centrifugation leaving a protein extract, and dialyzing the protein extract so obtained in a tris-buffered saline solution which contains the protease inhibitor, PMSF, at substantial concentration (1 mM). The extract is then applied to a DEAE - sepharose ion-exchange column which is eluted with a salt gradient. The eluate is dialyzed and then passed to a dye ligand chromatography column (Affi-gel Blue (Bio-Rad)) and eluted with a high concentration of urea in the presence of a detergent to produce the 69K protein. As with the Novotny et al and Brennan et al methods, this method is also not suitable to commercial production of the 69K protein because it requires the presence of protease inhibitors at substantial concentration (e.g. 1 mM PMSF) throughout the process to preserve the 69K protein from proteolytic degradation. For adaptation to large scale, the use of large volumes of buffers containing such toxic and expensive substances is a disadvantage, and the complete removal of these substances from the final product must be assured. In addition, the urea and detergent materials used to elute the protein from the dye ligand column may adversely affect the protein structure via denaturation.

Accordingly, it is a object of the present invention to provide an improved process for the extraction and purification of 69K protein from whole *B. pertussis* cells, which process is suitable to commercial production of the protein. It is another object to provide a process in which the yield of protein is increased. It is another object to provide a process in which the stability of the 69K protein is increased. It is a further object to provide a process in which toxic protease inhibitors or harsh denaturing agents such as a high concentration of urea are not employed.

SUMMARY OF THE INVENTION

The present invention provides a process for the extraction, purification and recovery of the 69K protein from whole *B. pertussis* cells which is well suited to commercial scale production, and represents a substantial improvement over prior methods, especially in terms of an enhanced yield and stability of the protein. In particular, the process of the present invention provides enhanced yield and stability of the 69K protein by inactivation of the *B. pertussis* cells via contact with a bacteriostatic agent prior to extraction of the protein from the cells. Inactivation in this manner stabilizes the 69K protein against degradation and eliminates the necessity of utilizing protease inhibitors. Surprisingly, inactivation in this manner also results in increased yield of 69K protein.

In addition, the process of the present invention provides enhanced yield of the protein by repetitive extraction of the protein from *B. pertussis* cells. Repetitive extraction provides increased yields when conducted with either live or inactivated cells, however, it has been found that the best yields are obtained when inactivated cells are utilized. Repetitive extraction includes a plurality of extraction steps, each extraction step encompassing suspending the cells in an aqueous medium which preferably includes a buffer, incubating the cells at a temperature of about 45° C. to about 65° C. for about 30 min. to about 1.5 hrs. to release proteins from the cells, followed by separating the released proteins from the cells to obtain a protein extract. The remaining cells are resuspended in a fresh aqueous medium and the incubation and separation steps repeated for as many times as necessary to obtain the majority of the 69K protein from the cells.

Finally, the process of the present invention provides an improved purification arrangement in which 69K protein is purified and recovered from a protein extract by dye ligand chromatography followed by chromatofocusing. In particular, the protein extract is first partially purified by using dye ligand chromatography which selectively binds the 69K protein and a limited number of other proteins but allows the large majority of contaminating proteins and other contaminants to be separated by passing through the column. The 69K protein is then completely separated from the limited number of other proteins eluted from the dye ligand chromatographic column by a chromatofocusing operation which separates proteins by differential binding and elution based upon differences in isoelectric points. Unexpectedly, the particular order of dye ligand chromatography followed by chromatofocusing allows maximization of column capacity, making this arrangement particularly suited for commercial scale up.

The process described thus represents a simple, reliable procedure where the yield of the protein is enhanced both by the stability during purification and the efficiency of extraction. In addition, the time required for recovery of the 69K protein is minimized as a result of the minimal use of dialysis steps. Also, the chromatographic procedures are employed in a particular order resulting in unexpected maximization of column capacity and faster loading and elution. Therefore, the process of this invention provides a method that is less time consuming and less expensive than currently known methods and is ideally suited for commercial production.

DESCRIPTION OF THE PREFERRED EMBODIMENTS

The process of the present invention is believed to be suitable for extracting and purifying 69K protein from all 69K producing strains of *Bordetella pertussis*. The 69K protein can be purified from any virulent strain of *Bordetella pertussis* grown under conditions where virulence factors are expressed. Suitable strains are, for example, phase I cultures of *B. pertussis* Tohama I, 165, 18323, or others, including clinical isolates and strains used for production of whole-cell pertussis vaccine. It is contemplated that proteins related antigenically to the 69K protein, including, for example, the *B. bronchiseptica* 68K protein and the *B. parapertussis* 70K protein could also be extracted and purified from these Bordetella species by the methods described herein. Furthermore, it is contemplated that recombinant versions of 69K protein could be purified using the described methods, after extraction from genetically engineered cells used to express the protein, for example *Escherichia coli, Bacillus, Streptomyces,* yeast, mammalian cell cultures, or others.

Growth of virulent B. pertussis in culture medium is well known, and previously described culture conditions are generally appropriate. Growth can be carried out in any medium suitable for phase I strains, for example, Cohen-Wheeler, Stainer-Scholte, Verwey, or others. Cultures can be grown under static conditions, in shaken cultures, or in vessels used for submerged fermentation, at a temperature which is compatible with expression of virulence factors; for example 30° C. to 37° C., especially 37° C. Cultures should be grown for a period of time which allows growth to at least the mid-logarithmic phase but not longer than to mid-stationary phase; for example 24 hours in fermenter cultures.

A growing culture of *Bordetella pertussis* or equivalent cells is inactivated according to the present invention by addition of a bacteriostatic agent, preferably of the type which exhibit the inhibitory properties of heavy metal compounds. Particularly preferred is the class of bacteriostatic agents known as "mercurials," including thimerosal, mercuric chloride, and various organic or inorganic mercury-containing compounds. Thimerosal can be used to inactivate a growing culture by adding it to the culture to a final concentration of 0.005 to 0.2% (weight/volume of culture), preferably 0.02%. Exposure to thimerosal may occur at any suitable conditions, however, exposure for 12 to 18 hours, at temperatures from 37° C. to 10° C. is preferred. The inactivated cells are then separated from the growth medium by any physical method, preferably by centrifugation and recovery of the sedimented cells.

It is particularly preferred to inactivate cells with 0.02% thimerosal (USP, XX, p 791, 1980) prior to extraction of 69K protein. Cells which have been previously inactivated with 0.02% Thimerosal are available commercially and may also be employed. No particular problems with the proteolytic degradation of the protein during purification have been observed when inactivated cells are employed. While not wishing to be bound by any theory, it appears that the initial inactivation of the cells with thimerosal has some benefit in stabilizing the 69K protein or inhibiting proteolytic enzymes throughout the remainder of the extraction and purification steps. Therefore, yields are increased as proteolytic enzymes do not destroy the protein. Also, the increased stability of the 69K protein avoids the need for expensive and toxic protease inhibitors as required by other known methods.

The unexpected advantage gained from inactivating cells prior to extraction and purification of 69K protein is demonstrated by Example 1 and 2, the results of which are reported in Table 1. Example 2 represented an attempt to purify 69K from live cells, in the absence of protease inhibitors. In this Example, 0.8 μg of the protein per gram wet weight of cells was finally recovered. Example 1 used cells inactivated with thimerosal. In this Example 196 μg of 69K per gram wet weight of cells was recovered. Part of the difference may be attributed to the more efficient repetitive extraction procedure which was used for the inactivated cells in Example 1, but not for the live cells in Example 2. However, it can be estimated that repetitive extraction increases the release of 69 K from cells at least 2.7-fold over a single extraction, as shown in Table 2, Examples 1 and 7. Thus, if a single extraction were employed, the yield from inactivated cells in Example 1 would be expected to be approximately 73 μg per gram wet weight of cells, rather then the 196 μg actually recovered. However, this result still represents an unexpected 90-fold improvement in final yield using inactivated cells rather than live cells. The beneficial effect on yield of inactivating cells with thimerosal prior to purification of 69K protein was totally unexpected. The effectiveness of thimerosal as a bacteriostatic agent is based on its content of a mercury-containing compound. Mercury and other heavy metals are known inhibitors of many kinds of enzymatic reactions. It is hypothesized that the apparent protection of 69K from degradation after thimerosal inactivation of cells could be the result of mercury inhibitation of proteolytic enzymes in the cell extract. Thus, in this respect, thimerosal is representative of the general class of bacteriostatic agents known as "mercurials" and also other agents based on other heavy metal compounds, which would be expected to be beneficial as well. While cells could be inactivated by heat or by treatment with other kinds of chemical agents such as azide or other respiratory poisons, these treatments would be unlikely to have the benefit of preventing proteolytic degradation.

Extraction of 69K protein from the cell surface of *B. pertussis* cells is accomplished, as reported by Brennan et al. by suspending wet cell material initially separated from a culture of cells in a buffer, incubating the cell suspension to release protein and separating the proteins so released by centrifugation to obtain a protein extract. Brennan et al discloses one extraction step of this type. However, this single extraction step has been found to be relatively inefficient in that a considerable portion of the total amount of 69K protein is not released. Unexpectedly, repetitive extraction incorporating a plurality of extraction steps, has been found to result in the release of significant additional amounts of 69 K protein. Referring to Table 2, three repetitions of the extraction step, each consisting of 90 minutes at 60° C., results in the release of 570 μg. of 69K protein per gram wet cell weight (Example 1) as compared to the release of only 212 μg 69K protein per gram wet cell weight for a single extraction for 4.5 hours (Example 7). Therefore, the amount released is unexpectedly higher for repetition rather than for the increased time of extraction. It is estimated by immunoassay and by SDS-PAGE, that less than 1% of the total protein of *B. pertussis* cells is 69K protein. Therefore the initial extraction of 570 μg per gram wet weight (equivalent to 0.46% of the total cell protein) is indicative of an extremely efficient method of releasing 69K protein from cells. While not wishing to be bound by any theory, it is believed that the yield of 69K protein in the extract is greatly increased by the repetitive extraction process, because the replenishing of the extract with fresh aqueous medium and preferably fresh buffer can overcome a set of conditions which may have become limiting to 69K protein release in the initial incubation.

Repetitive extraction according to the present invention includes a plurality of extraction steps in series. Each step is similar to the single extraction disclosed by Brennan et al and encompasses suspending cells in an aqueous medium, incubating the cell suspension to release proteins into solution in the aqueous medium and separating the protein so released to obtain a protein extract. The proteins are separated from the cells by any physical means preferably centrifugation. The protein containing supernatant is saved and the cells remaining after separation of the protein extract are resuspended in a fresh aqueous medium and the incubation and separation portions repeated to release and recover additional protein extract. Three repetitions are preferred, although it is contemplated that some additional protein may be recovered from further repetitions.

Repetitive extraction of the protein may be accomplished by elevated temperature over a fairly broad temperature and time range. An effective useful temperature range of 37° C. to 70° C., preferably 60° C., is contemplated. The length of each incubation can be adjusted to any effective time from 30 minutes to 2 hours, preferably 90 minutes. It is contemplated that each extraction step employ effective time and temperature conditions which may be the same or different from step to step.

Repetitive extraction may be accomplished by suspending the *B. pertussis* cell material in any aqueous medium prior to incubation. A preferred aqueous medium is a buffer solution, adjusted to pH 7 to 8. A particularly preferred aqueous medium is 0.01 M phosphate buffered saline, employed at a concentration of approximately 5 volumes aqueous medium per volume of wet cell material.

The protein extract material is then precipitated with polyethylene glycol. Polyethylene glycol, at a concentration of 30% (weight/volume), is added to the protein extract to give a precipitate fraction rich in 69K protein. Other reagents commonly used to precipitate proteins whould also be suitable, e.g. ammonium sulfate or organic solvents such as ethanol or acetone. The immediate precipitation of the proteins from the protein extract may be beneficial for separating the 69K protein from other substances in the extract that could adversely effect its stability. In addition, the immediate precipitation allows rapid continuation of the process to the chromatography steps by redissolving the protein extract in the desired buffer in a concentrated form without the lengthy dialysis procedures that would otherwise be required.

The 69K protein is recovered from the precipitated, extract protein by dye ligand chromatography followed by chromatofocusing. Unexpectedly, it has been found that use of a dye ligand chromatographic column as the first purification step takes advantage of the selective binding of only some proteins, including 69K, to this material. The large majority of contaminating proteins and other contaminants are therefore removed from the protein extract, as most of them do not bind and simply pass through. Some of the contaminants which do bind can be further separated from the 69K protein by differential elution from the dye ligand column with a gradient of eluant concentration. Another advantage of dye ligand chromatography at this stage of the process is its capacity; since most of the proteins do not bind, a relatively small column can be used for chromatography of the extract originating from a large amount of cells. For example, thirty ml of gel is sufficient for the extract from at least 120 g wet weight of cells. The selectivity and high capacity allows the use of relatively small dye ligand chromatographic columns with resultant rapid loading and elution.

Suitable dye ligand chromatographic matrixes include those affinity matrixes containing a protein specific binding medium, such as a dye, which binds to the 69K protein of *B pertussis*. Particularly useful are those dye ligands which are organic molecules having a structure similar to nucleotides. Exemplary of such matrixes are Affi-gel Blue (Bio-Rad), Blue-Sepharose CL-6B, Red Sepharose CL-6B (Pharmacia).

To accomplish the dye ligand chromatography, the precipitated protein extract is redissolved in a buffer solution of low ionic strength in the pH range of approximately 6 to 8.5, preferably a tris-hydroxymethylamino methane (tris) solution of 0.05M at pH 7.4. The dissolved protein extract precipitate is then applied to a chromatography column packed with a matrix such as Affi-gel Blue (Bio-Rad), Blue Sepharose CL-6B, Red Sepharose CL-6B (Pharmacia) or other dye-ligand gel, preferably Affi-gel Blue, equilibrated in the above buffer. After the protein extract precipitate has been loaded onto the column, the column is washed with the equilibration buffer. The 69K protein, which has bound to the column, is then eluted with a solution of a salt or other substance which disrupts the protein-ligand interaction. The eluant can be a salt such as $MgCl_2$, NaCl, KCl, or others. Other eluants such as KSCN or urea, acting as chaotropic agents, could also be used. Alternatively, a biospecific compound such as AND+, ATP, or other nucleotide could be used as an eluant. Preferably $MgCl_2$ is used, as it is inexpensive and, at low concentration, unlikely to adversely affect the structure of the protein. Furthermore, the $MgCl_2$ eluant is preferably used in a linear concentration gradient from 0 to 0.5M, which further separates the 69K from contaminants by differential elution at increasing $Mg^{++}$ concentration. The presence of 69K protein in the eluted fractions can be monitored by electrophoretic analysis of samples or by specific assays to 69K protein such as ELISA or dot blot immunoassays with anti-69K antibodies.

The 69K protein-containing eluate from the dye ligand chromatographic step is dialyzed to remove the $MgCl_2$ and to prepare the eluate in the appropriate buffer for the chromatofocusing step to follow. Other methods might also be used, for example, diafiltration on a desalting gel column. The fractions which contain 69K protein eluted from the Affi-gel Blue column as determined by electrophoresis, specific immunoassays or any other suitable means are pooled and then dialyzed against a low ionic strength and high pH buffer preferably 0.025M ethanolamine/acetate pH 9.4.

The final purification utilizes a chromatofocusing matrix of the type which binds proteins at high pH and elutes with a decreasing pH gradient. The chromatofocusing operation is particularly effective as the final purification step for the recovery of 69K protein. A fairly small column has sufficient capacity for the partially-purified material originating from a large quantity of cells. A chromatography column is packed with a chromatofocusing gel such as Polybuffer Exchanger Gel PBE 94 (Pharmacia), equilibrated in low ionic strength/high pH buffer, preferably 0.025M ethanolamine/acetate pH 9.4. The dialyzed eluate from the dye ligand chromatographic step is loaded onto the column and then the column is washed with one bed volume of equilibration buffer. The bound protein is eluted with a gradient of decreasing pH (from 9.4 to 6.0) which is achieved by passing through the column approximately 12 bed volumes of a 1/10 dilution of Polybuffer 96 (Pharmacia) adjusted to pH 6 with acetic acid. Analysis of fractions eluted from the column by SDS-PAGE and staining with Coomassie Blue shows that the 69K is effectively separated from the remaining contaminants by the chromatofocusing column, and the protein is reproducibly eluted as two peaks, at pH 7.2 and 6.5, corresponding to isoelectric variants of the same protein. The process results in a purified 69K preparation of high purity which is essentially free of contamination with bacterial endotoxin.

While the Pharmacia PBE gel with the polybuffer eluant system is a convenient, commercially available material, it is contemplated that the final purification of 69K protein could by achieved by any ion-exchange gel system which binds proteins at high pH and allows their elution in a decreasing pH gradient.

The pure 69K material produced according to the process of the present invention may be utilized to produce an acellular *B. pertussis* vaccine formulation for inducing immunity to whooping cough in mammals. The 69K protein may be thus incorporated with a pharmaceutically acceptable carrier such as any suitable liquid media. An example of such a carrier is saline solution. The antigenic protein may be in solution or suspended as a solid in the carrier. The vaccine formulation may also comprise an adjuvant for stimulating the immune response and thereby enhancing the effect of the vaccine. Convenient adjuvants for use in the present invention include, for example, aluminum hydroxide and aluminum phosphate. Conveniently the vaccine formulations are presented to contain a final concentration of antigenic protein in the range of from 0.01 to 5 mg/ml, preferably 0.03 to 2 mg/ml, most preferably 0.3 mg/ml. After formulation the vaccine may be incorporated into a sterile container which is then sealed and stored at a low temperature, for example 4° C. or may be freeze-dried. In order to induce immunity in man to whooping cough one or more doses of the vaccine suitably formulated may be administered. It is recommended that each dose is 0.1 to 2 ml preferably 0.2 to 1 ml, most preferably 0.5 ml of vaccine. The present invention, in a further aspect provides a method for inducing immunity to whooping cough in mammals including man, comprising the administration of an effective amount of a vaccine formulation, as hereinbefore defined, to the host. The vaccines of the present invention may be administered by any conventional method for the administration of vaccines including oral and parentoral (e.g., subcutaneous or intramuscular) injection. The treatment may consist of a single dose of vaccine or a plurality of doses over a period of time. Vaccines according to the present invention may also comprise one or more other antigenic components such as, for example, suitably toxoided LPF, to reduce the likelihood of mutant strains of *B. pertussis* avoiding the concomitant immune response.

The pure 69K material produced according to the process of the present invention may also be utilized for analytical or diagnostic purposes in the evaluation of immune responses to disease or vaccination. For example, the ELISA technique (enzyme-linked immunsorbent assay) for detection of specific antibodies requires a source of the relevant antigen. The 69K protein purified according to the proces of the present invention is free of contaminants, and would thus be a desirable protein preparation to use in ELISA for unambiguous detection and quantitation of antibodies directed against 69K protein. It could also be used in any other immunological method requiring a purified antigen for the measurement of immune responses. Likewise purified 69K could be used as an immunogen for development of specific antibodies which could then be used in other immunological applications of diagnostic methods involving specific recognition of 69K protein.

The following examples are illustrative of the process of the present invention, without limiting same:

EXAMPLE 1

Inactivated Cells

Cell surface extract

*Bordetella pertussis*, Lederle strain 130, is grown in liquid Stainer-Scholte medium [Stainer, D. W. and Scholte, M. J. 1971 J. Gen. Microbiol. 63: 211–220] and inactivated with 0.02% thimerosal. The thimersoal is added to the culture when the culture is at a temperature of 37° C. and inactivation occurs overnight during which the temperature is lowered to 10°–15° C. The inactivated cells are recovered by centrifugation and the wet cell paste (112 g) is suspended in 0.01M phosphate-buffered saline pH 7.2 (PBS) to a final volume of 640 ml. The suspension is incubated at 60° C. for 90 minutes; then the cells are removed by centrifugation and the supernatant is saved at 4° C. The cells are again suspended in phosphate-buffered saline (PBS) to a final volume of 640 ml, incubated at 60° C. for 90 minutes, and the cells are removed by centrifugation. The supernatant from this second incubation is combined with the first supernatant and stored at 4° C. The cells are resuspended, as described above, a third time in phosphate-buffered saline, incubated and the cells centrifuged out. The third supernatant is combined with the first two at 4° C. The proteins in the combined supernatant pool are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 830 ml of buffer consisting of 0.05M tris pH 7.4 (buffer A). This protein solution represents the cell surface extract (CSE).

The concentration of 69K protein in the CSE is measured by a dot blot immunoassay, where serially-diluted samples and pure 69K standard are spotted on to a nitrocellulose membrane, and reacted first with specific anti-69K antibody, then with a peroxidase-conjugated second antibody, and finally with a reagent (4-chloro-1-naphthol) which develops a color in the presence of peroxide and peroxidase. The results of the immunoassay are consistent with measurements based on the relative proportion of a 69K band in samples run on SDS-PAGE. As measured by the dot blot immunoassay, the 69K content of CSE is 570 μg 69K per gram wet weight of cells used to prepare the CSE.

Dye-ligand chromatography of cell surface extract

An Affi-gel Blue chromatography support (Bio-Rad) is washed and equilibrated in buffer A, and packed into a column of about 2.5×9 cm (about 30 ml bed volume). The 830 ml cell surface extract is applied to the column, followed by a wash with one bed volume of buffer A. The column is eluted first with a linear gradient of from 0 to 0.5M magnesium chloride in buffer A (50 ml each) followed by a wash with 30 ml of 0.5M magnesium chloride. Finally, 50 ml of 2M magnesium chloride is passed through the column. The protein in the eluate is monitored by absorbance at 280 nm. A prominent peak is observed upon elution with the magnesium chloride gradient. Analysis of the fractions by SDS-PAGE shows the 69K protein greatly enriched in the fractions representing the eluate peak. These are combined and dialyzed against 0.025M ethanolamine/acetate pH 9.4 (buffer B).

Chromatofocusing

The chromatofocusing support is Polybuffer exchanger PBE 94 (Pharmacia) equilibrated in buffer B and packed in a column of 1.7×15 cm (about 35 ml gel). The dialyzed eluate pool from the Affi-gel Blue column (about 135 ml) is loaded onto the PBE column, followed by a wash with one bed volume of buffer B. The column is eluted with a self-forming gradient (pH 9.4 to 6.0) by passing through 400 ml of a 1/10 dilution of Polybuffer 96 (Pharmacia) adjusted to pH 6 with acetic acid. Some protein (monitored by A280) was not retained by the column. The pH gradient results in elution of several peaks, most prominently at pH 7.2 and 6.5. SDS-PAGE and Western blot with anti-69K antibody showed the protein in these two eluate peaks to be 69K protein of high purity. To remove the Polybuffer salts, the protein in the pooled fractions is precipitated by addition of solid ammonium sulfate, 0.7 g per ml of eluate, and the precipitate is recovered by centrifugation at 10,000 rpm for 20 minutes. The pellet is redissolved in a minimal volume of phosphate-buffered saline. The yield of pure 69K protein from this process is 22 mg, or about 196 μg per gram wet weight of starting cell material. Thus the efficiency of recovery from the initial CSE extract is about 35% (196 μg÷570 μg). The bacterial endotoxin in the purified protein, measured by Limulus amoebocyte lysate (LAL) assay, is 0.06 EU/μg of protein.

EXAMPLE 2

Live Cells

Cell surface extract

*Bordetella pertussis*, Lederle strain 130, is grown in liquid Stainer-Scholte medium and not inactivated. The cells are recovered by centrifugation and the wet cell paste (26 g) is suspended in phosphate-buffered saline (PBS) to a final volume of 62 ml. The suspension is incubated at 60° C. for 90 minutes; then the cells are removed by centrifugation and the supernatant is saved at 4° C. The proteins in the supernatant are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 22 ml of buffer consisting of 0.05M tris pH 7.4 (buffer A). This protein solution represents the cell surface extract (CSE).

Dye-ligand chromatography of cell surface extract

An Affi-gel Blue chromatography support (Bio-Rad) is washed and equilibrated in buffer A, and packed into a column of about 1.7×9 cm (about 20 ml bed volume). The 22 ml cell surface extract is applied to the column, followed by a wash with one bed volume of buffer A. The column is eluted first with a linear gradient of from 0 to 0.5M magnesium chloride in buffer A (50 ml each) followed by a wash with 30 ml of 0.5M magnesium chloride. Finally, 50 ml of 2M magnesium chloride is passed through the column. The protein in the eluate is monitored by absorbance at 280 nm. A small peak is observed upon elution with the magnesium chloride gradient. Analysis of the fractions by SDS-PAGE shows the 69K protein present in the fractions representing the eluate peak. These are combined and dialyzed against 0.025M ethanolamine/acetate pH 9.4 (buffer B).

Chromatofocusing

The chromatofocusing support is Polybuffer exchanger PBE 94 (Pharmacia) equilibrated in buffer B and packed in a column of 0.9×5 cm (about 3 ml gel). The dialyzed eluate pool from the Affi-gel Blue column (about 24 ml) is loaded onto the PBE column, followed by a wash with one bed volume of buffer B. The column is eluted with a self-forming gradient (pH 9.4 to 6.0) by passing through 60 ml of a 1/10 dilution of Polybuffer 96 (Pharmacia) adjusted to pH 6 with acetic acid. Some protein (monitored by A280) was not retained by the column. The pH gradient results in elution of peaks at pH 7.2 and 6.5. SDS-PAGE and Western blot with anti-69K antibody showed the protein in these two eluate peaks to be 69K protein of high purity, but the concentration was so low that it was not detected without first concentrating the sample about 30-fold by lyophilization. The yield of pure 69K protein from this process is 0.02 mg, or about 0.8 μg per gram wet weight of starting cell material.

TABLE 1

| Effect of Inactivation on Final Recovery of 69K protein. | |
|---|---|
| Example | Final Recovery, μg per g wet weight of cells |
| 1 | 196 |

TABLE 1-continued

| Effect of Inactivation on Final Recovery of 69K protein. | |
|---|---|
| Example | Final Recovery, μg per g wet weight of cells |
| 2 | 0.8 |

EXAMPLE 3
Cell surface extract

*Bordetella pertussis*, Lederle strain 130, is grown in liquid Stainer-Scholte medium and inactivated with 0.02% thimerosal. The cells are recovered by centrifugation and the wet cell paste (37g) is suspended in phosphate-buffered saline (PBS) to a final volume of 213 ml. The suspension is incubated at 25° C. for 16 hours; then the cells are removed by centrifugation and the supernatant is saved at 4° C. The proteins in the supernatant pool are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 32 ml of buffer consisting of 0.05M tris pH 7.4 (buffer A). This protein solution represents the cell surface extract (CSE). The concentration of 69K protein in the CSE is measured by dot blot immunoassay as in Example 1 and by SDS-PAGE analysis to be 7.5 μg per gram wet weight of starting cell material.

EXAMPLE 4

Cell surface extract

*Bordetella pertussis,* Lederle strain 130, is grown in liquid Stainer-Scholte medium and inactivated with 0.02% thimerosal. The cells are recovered by centrifugation and the wet cell paste (37 g) is suspended in phosphate-buffered saline (PBS) to a final volume of 213 ml. The suspension is incubated at 37° C. for 16 hours; then the cells are removed by centrifugation and the supernatant is saved at 4° C. The proteins in the supernatant pool are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 69 ml of buffer consisting of 0.05M tris pH 7.4 (buffer A). This protein solution represents the cell surface extract (CSE). The concentration of 69K protein in the CSE is measured by dot immunoassay as in Example 1 and by SDS-PAGE analysis to be 53.4 μg per gram weight of starting cell material.

EXAMPLE 5

*Bordetella pertussis,* Lederle strain 130, is grown in liquid Stainer-Scholte medium and inactivated with 0.02% thimerosal. The cells are recovered by centrifugation and the wet cell paste (11.3 g) is suspended in phosphate-buffered saline (PBS) to a final volume of 65 ml. The suspension is incubated at 50° C. for 60 minutes; then the cells are removed by centrifugation and the supernatant is saved at 4° C. The proteins in the supernatant pool are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 8 ml of buffer consisting of 0.05M tris pH 7.4 (buffer A). This protein solution represents the cell surface extract (CSE). The concentration of 69K protein in the CSE is determined by measuring the total protein content by commercial protein assay kit (Bio-Rad), then using SDS-PAGE analysis to measure the percentage of the total which appears as a 69K band in stained gels. The concentration is thus found to be 161 μg per gram wet weight of starting cells.

EXAMPLE 6

Cell surface extract

*Bordetella pertussis,* Lederle strain 130, is grown in liquid Stainer-Scholte medium and inactivated with 0.02% thimerosal. The cells are recovered by centrifugation and the wet cell paste (11.3 g) is suspended in phosphate-buffered saline (PBS) to a final volume of 65 ml. The suspension is incubated at 50° C. for 60 minutes; then the cells are removed by centrifugation and the supernatant is saved at 4° C. The cells are again suspended in phosphate-buffered saline (PBS) to a final volume of 65 ml, incubated at 50° C. for 60 minutes, and the cells are removed by centrifugation. The supernatant from this second incubation is kept separate from the first supernatant and stored at 4° C. The cells are resuspended, as described above, a third time in phosphate-buffered saline, incubated and the cells centrifuged out. The third supernatant is kept separate from the first two at 4° C. The proteins in each supernatant pool are precipitated by gradual addition, with stirring, of solid polyethylene glycol (PEG, MW 8000) to a final concentration of 30% (weight/volume). The resulting precipitates are recovered by centrifugation (10,000 rpm, 20 minutes) and the supernatants are discarded. The pellets are each redissolved in 8 ml of buffer consisting of 0.05M tris pH 7.4 (buffer A). Each redissolved percipitate is analyzed for protein content and 69K content as in Example 5. The three solutions are then pooled and this pool represents the complete cell surface extract (CSE). The total recovery of 69K protein is thus measured to be 271 μg per gram wet weight of starting cell material.

EXAMPLE 7

Cell surface extract

*Bordetella pertussis,* Lederle strain 130, is grown in liquid Stainer-Scholte medium and inactivated with 0.02% thimerosal. The cells are recovered by centrifugation and the wet cell paste (37 g) is suspended in phosphate-buffered saline (PBS) to a final volume of 213 ml. The suspension is incubated at 60° C. for 4.5 hours; then the cells are removed by centrifugation and the supernatant is saved at 4° C. The proteins in the supernatant pool are precipitated by gradual addition, with stirring, of solid polyethylene glycol (PEG, MW 8000) to a final concentration of 30% (weight/volume). The resulting precipitate is recovered by centrifugation (10,000 rpm, 20 minutes) and the supernatant is discarded. The pellet is redissolved in 103 ml of buffer consisting of 0.05M tris pH 7.4 (buffer A). This protein solution represents the cell surface extract (CSE). The concentration of 69K protein in the CSE is measured by dot blot immunoassay as in Example 1 and by SDS-PAGE to be 212 μg per gram wet weight of starting cell material.

TABLE 2

| Effect of Repetitive Extraction on yields of 69K protein. | | | |
|---|---|---|---|
| Example | Temp. | Time/(Hrs.) | Yield 69K present in CSE μg/g wet cell weight |
| 3 | 25° C. | 16 | 7.5 |
| 4 | 37° C. | 16 | 53.4 |
| 5 | 50° C. | 1 | 161.5 |
| 6 | 50° C. | 3 × 1* | 270.3 |
| 7 | 60° C. | 4.5 | 212 |
| 1 | 60° C. | 3 × 1.5* | 570.4 |

*3 repetitive extractions

I claim:

1. A process for extracting and purifying an outer membrane protein having a molecular weight of about 69,000 daltons from *Bordetella pertussis* cells which comprises: inactivating the *Bordetella pertussis* cells by contacting said cells with a mercurial bacteriostatic agent; obtaining a protein extract from said inactivated cells by suspending the cells in a aqueous medium, incubating the cell suspension to release proteins from the cells and separating the released proteins from the cells after incubation; separating said outer membrane protein having a molecular weight of about 69,000 daltons from said protein extract by applying said protein extract to a dye ligand chromatographic support; eluting proteins bound to the dye ligand support, applying the eluate from said dye ligand support to a chromatofocusing support and recovering said outer membrane protein therefrom.

2. The process of claim 1 wherein said mercurial bacteriostatic agent comprises thimersol or mercuric chloride.

3. The process of claim 1 wherein said mercurial bacteriostatic agent comprises thimersol.

4. The process of claim 3 wherein said *Bordetella pertussis* is inactivated by contacting with thimersosal at a concentration of 0.01 to 0.05% (weight/volume of culture).

5. The process of claim 4 wherein said thimerosol in employed at a concentration of 0.02% (weight/volume of culture).

6. The process of claim 1 wherein said aqueous medium comprises a buffer having a pH of from about 5 to about 9.

7. The process of claim 6 wherein said buffer comprises 0.01M phosphate buffered saline.

8. The process of claim 1 wherein said dye ligand chromatographic support is eluted with a linear gradient comprising up to about 2.5M magnesium chloride in a buffer.

9. The process of claim 1 wherein said eluate from said dye ligand chromatographic support is dialyzed with an ethanolamine/acetate buffer having pH 9.4 prior to application to said chromatofocusing support.

10. The process of claim 1 wherein said incubation is conducted at a temperature of from about 45° C. to about 60° C. and for a time of from about 30 to about 90 minutes.

11. The process of claim 1 wherein said protein extract is separated by centrifuge with the supernatant retained.

12. The process of claim 11 wherein the supernatent is precipitated with ammonium sulfate, ethanol or acetone.

13. The process of claim 1 wherein the supernatent is precipitated with polyethylene glycol.

14. The process of claim 13 wherein said polyethylene glycol is employed at a concentration of from about 20 to 40% weight/volume.

15. The process of claim 1 wherein said dye ligand chromatographic support comprises Affi-gel Blue.

16. The process of claim 1 wherein said outer membrane protein is recovered from said chromatofocusing support by eluting with a self formed pH gradient.

* * * * *